United States Patent [19]

Long et al.

[11] Patent Number: 4,612,406
[45] Date of Patent: Sep. 16, 1986

[54] OLEFIN OLIGOMERIZATION

[75] Inventors: Gary N. Long, Putnam Valley; Regis J. Pellet, Croton-on-Hudson; Jule A. Rabo, Armonk, all of N.Y.

[73] Assignee: Union Carbide Corporation, Danbury, Conn.

[21] Appl. No.: 732,134

[22] Filed: May 9, 1985

Related U.S. Application Data

[62] Division of Ser. No. 551,881, Nov. 15, 1983, Pat. No. 4,528,414.

[51] Int. Cl.$^4$ .............................................. C07C 2/04
[52] U.S. Cl. .................................... 585/329; 585/322; 585/415; 585/514; 585/510; 585/528; 585/532; 585/640
[58] Field of Search ............... 585/322, 329, 415, 514, 585/510, 310, 528, 532, 640

[56] References Cited

U.S. PATENT DOCUMENTS

| | | | |
|---|---|---|---|
| 3,756,942 | 9/1973 | Cattanach | 208/137 |
| 3,760,024 | 9/1973 | Cattanach | 260/673 |
| 3,775,501 | 11/1973 | Kaeding et al. | 260/673 |
| 3,827,968 | 8/1974 | Givens et al. | 208/49 |
| 4,021,502 | 5/1977 | Plank et al. | 260/683 |
| 4,150,062 | 4/1979 | Garwood et al. | 260/673 |
| 4,227,992 | 10/1980 | Garwood et al. | 208/46 |
| 4,254,295 | 3/1981 | Tabak | 585/533 |
| 4,310,440 | 1/1982 | Wilson et al. | 502/208 |
| 4,392,984 | 7/1983 | Engelbach et al. | 252/432 |
| 4,499,315 | 2/1985 | Garska et al. | 585/415 |
| 4,499,316 | 2/1985 | Garska et al. | 585/415 |
| 4,527,001 | 7/1985 | Kaiser | 585/642 |
| 4,551,236 | 11/1985 | Lok et al. | 208/112 |
| 4,554,143 | 11/1985 | Messina et al. | 423/306 |
| 4,567,029 | 1/1986 | Wilson et al. | 423/306 |

Primary Examiner—Andrew H. Metz
Assistant Examiner—A. Pal
Attorney, Agent, or Firm—Gary L. Warner

[57] ABSTRACT

The process for the oligomerization of linear and/or branched chain $C_2$ to $C_{12}$ olefins with non-zeolitic molecular sieves having a framework structure of $MO_2$, $AlO_2$ and $PO_2$ tetrahedra and having an empirical chemical composition on an anhydrous basis expressed by the formula

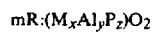

$$mR:(M_xAl_yP_z)O_2$$

wherein "R" represents at least one organic templating agent present in the intracrystalline pore system; "m" represents the moles of "R" present per mole of $(M_xAl_yP_z)O_2$, "M" represents silicon, iron, titanium or at least one of magnesium, manganese, cobalt and zinc such being present in the form of a tetrahedral oxide; "x", "y" and "z" represent the mole fractions of "M", aluminum and phosphorous, respectively.

31 Claims, 2 Drawing Figures

OLEFIN OLIGOMERIZATION

This application is a division of prior U.S. application: Ser. No. 551,881, Filing Date, Nov. 15, 1983, now U.S. Pat. No. 4,528,414.

FIELD OF THE INVENTION

The instant invention relates to the use of new non-zeolitic molecular sieves for the oligomerization of linear and/or branched chain $C_2$ to $C_{12}$ olefins whereby relatively low value olefin feedstocks are upgraded to products having substantially greater economic value.

BACKGROUND OF THE INVENTION

Processes for the conversion of low molecular weight olefins are well known in the prior art. Representative of some of the early work in this area are U.S. Pat. Nos.: 3,140,249; 3,140,251; 3,140,253; 3,140,322; and 2,972,643.

The conversion of paraffins, olefins and/or naphthenes to aromatics using a ZSM-5 catalyst is disclosed in U.S. Pat. No. 3,756,942. The conversion of olefins to aromatics by use of ZSM-5 and ZSM-8 is disclosed in U.S. Pat. No. 3,760,024. The prior art relating to olefin conversion over ZSM-type catalysts also includes numerous process related patents including: U.S. Pat. No. 3,775,501 (co-feed air with olefins over ZSM-5); U.S. Pat. No. 3,827,968 (ZSM-5 in a two step process); U.S. Pat. No. 3,960,978 (ion-exchange and/or steamed ZSM-5 or ZSM-11); U.S. Pat. No. 4,021,502 (olefin conversion using ZSM-5, ZSM-12, ZSM-18, chabazite and beta zeolite under controlled process conditions); U.S. Pat. No. 4,150,062 (use of co-fed water with olefins over ZSM-5); U.S. Pat. No. 4,227,992 (ethylene/propylene conversion over ZSM-12 employing controlled process conditions).

The above processes employ the aluminosilicates generally known as "ZSM-type" aluminosilicates. Accordingly, such processes do not relate to a process or processes employing non-zeolitic molecular sieves. The use of certain novel non-zeolitic molecular sieves as "polymerization" catalysts to produce high boiling polymerization products is disclosed in U.S. Pat. Nos. 4,440,871 (SAPOs), 4,500,651 (TAPOs) 4,567,029 (MeAPOs and MAPOs) and 4,554,143 (FAPOs). The oligomerization of linear and/or branched $C_2$ to $C_{12}$ olefins is not disclosed in the aforementioned patents. U.S. Pat. No. 4,310,440, discloses the aluminophosphates (AlPO$_4$) may be employed as polymerization catalysts.

SUMMARY OF THE INVENTION

Figure 1:
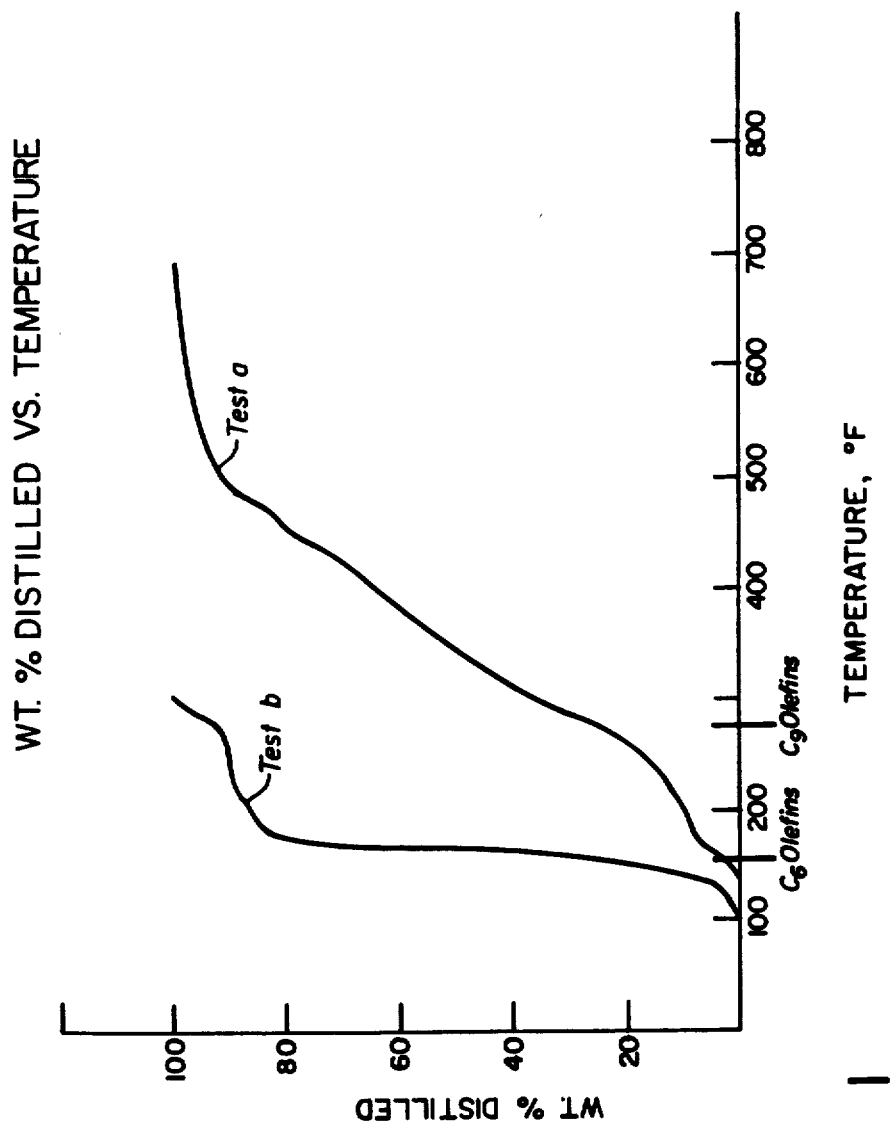
FIG. 1 shows the effect of water on the product distribution of the instant invention.

The instant process comprises the process for the oligomerization of linear and/or branched chain $C_2$ to $C_{12}$ olefins using non-zeolitic molecular sieves ("NZ-MS") having the framework structure of $MO_2$, $AlO_2$ and $PO_2$ tetrahedra and having an empirical chemical composition on an anhydrous basis expressed by he formula:

$$mR: (M_xAl_yP_z)O_2$$

wherein "R" represents at least one organic templating agent present in the intracrystalline pore system; "m" represents the moles of "R" present per mole of $(M_xAl_yP_z)O_2$, "M" represents silicon, iron, titanium or at least one of magnesium, manganese, cobalt and zinc, such being present in the form of a tetrahedral oxide and "x", "y" and "z" represent the mole fractions of "M", aluminum and phosphorus, respectively, present as tetrahedral oxides.

The non-zeolitic molecular sieves employed in the instant process are generally disclosed in U.S. Pat. Nos. 4,440,871 (SAPOs), 4,500,651 (TAPOs), 4,567,029 (MeAPOs and MAPOs) and 4,544,143 (FAPOs). The aforementioned patents are incorporated herein by reference thereto. The acroyns SAPO, TAPO, MeAPO, MAPO and FAPO are explained in the aforementioned patents and are discussed hereinafter in the "DETAILED DESCRIPTION OF THE INVENTION." The instant process comprises contacting linear and/or branched $C_2$ to $C_{12}$ olefins with at least one of the aforementioned non-zeolitic molecular sieves at effective conversion conditions. The preferred non-zeolitic molecular sieves of this invention are characterized by an adsorption of triethylamine of less than 5% by weight at a pressure of 2.6 torr and a temperature of 22° C.

DETAILED DESCRIPTION OF THE INVENTION

The instant process relates to the oligomerization of linear and/or branched $C_2$ to $C_{12}$ olefins or of a feedstock capable of forming such olefins in situ. The process involves contacting such olefins at effective conversion conditions with at least one non-zeolitic molecular sieve ("NZ-MS") having a framework structure of $MO_2$, $AlO_2$ and $PO_2$ tetrahedra and having an empirical chemical composition on an anhydrous basis expressed by the formula:

$$mR: (M_xAl_yP_z)O_2$$

wherein "R" represents at least one organic templating agent present in the intracrystalline pore system; "m" represents the moles of "R" present per mole of $(M_xAl_yP_z)O_2$, "M" represents silicon, iron, titanium or at least one of magnesium, manganese, cobalt and zinc, such being present in the form of a tetrahedral oxide; and "x", "y" and "z" represent the mole fractions of "m", aluminum and phosphorus, respectively, present as tetrahedral oxides.

The non-zeolitic molecular sieves are described in U.S. Pat. Nos. 4,440,871 (SAPOs), 4,500,651 (TAPOs), 4,567,029 (MeAPOs and MAPOs) and 4,544,143 (FAPOs) incorporated herein by reference thereto. These non-zeolitic molecular sieves may be employed herein to produce products comprising two or more of the original linear and/or branched olefins. The non-zeolitic molecular sieves are preferably characterized by an adsorption of triethylamine of less than 5% by weight at a pressure of 2.6 torr and a temperature of 22° and more preferably are also characterized by an adsorption of cyclohexane of at least 2% by weight at a pressure of a 90 torr and a temperature of 24° C.

In addition, the most preferred non-zeolitic molecular sieves are characterized by x-ray diffraction patterns as set forth in Table A, Table B or Table C:

TABLE A

| 2θ | d(Å) | Relative Intensity |
|---|---|---|
| 9.3–9.65 | 9.51–9.17 | m–s |
| 20.2–20.6 | 4.40–4.31 | m–s |
| 20.9–21.3 | 4.25–4.17 | s–vs |
| 22.0–22.5 | 4.04–3.95 | s–vs |
| 22.5–22.9 | 3.95–3.92 | m–s |
| 23.0–23.4 | 3.87–3.80 | m–s |

TABLE B

| 2θ | d(Å) | Relative Intensity |
|---|---|---|
| 8.5–8.6 | 10.40–10.28 | m–s |
| 20.2–20.3 | 4.40–4.37 | m |
| 21.9–22.1 | 4.06–4.02 | w–m |
| 22.6–22.7 | 3.93–3.92 | vs |
| 31.7–31.8 | 2.823–2.814 | w–m |

TABLE C

| 2θ | d(Å) | Relative Intensity |
|---|---|---|
| 13.6–13.8 | 6.51–6.42 | w–m |
| 20.5–20.6 | 4.33–4.31 | w–m |
| 21.1–21.3 | 4.21–4.17 | vs |
| 22.1–22.3 | 4.02–3.99 | m–s |
| 22.8–23.0 | 3.90–3.86 | m |
| 23.1–23.4 | 3.82–3.80 | w–m |
| 25.5–25.9 | 3.493–3.44 | w–m |

The class members of the molecular sieves set forth in the above identified pending applications are referred to therein by a series of abbreviations. These abbreviations include: SAPO, FeAPO, CoAPO, MAPO, MnAPO, TAPO, and ZAPO where each acronym is as defined in the above incorporated copending applications. The members of each class, e.g., the members of the SAPO class, MAPO class or ZAPO class, are characterized by referring to class members as SAPO-5, MnAPO-11, ZAPO-34, "ZAPO-n", "SAPO-n" and etc., wherein the "n" designation is a number specific to a given class member as its preparation is reported in the aforementioned copending applications. For the sake of convenient reference the aforementioned non-zeolitic molecular sieves, i.e., those disclosed in the above copending patent applications, will be generally referred to herein as the "NZ-MS" class of molecular seives. Individual members of the class of "NZ-MSs" will be referred to by the nomenclature assigned to that class member in a particular referenced copending application.

The conversion conditions employed in the instant process, such as temperature, pressure, space velocity and molar ratio of co-fed diluent to olefin reactants will affect the process and the products formed thereby. In general the process is carried out at effective process conditions, i.e., conversion conditions such that oligomerization of said starting olefin occurs, preferably such that at least 20 percent by weight of the starting olefin is oligomerized to products containing a higher carbon number than the starting olefin(s), more preferably at least 50 percent by weight and most preferably at least 70 percent by weight. Optimum conversion conditions are those in which motor fuel products are the major products, e.g. high octane gasoline component products (boiling between about 80° F. and about 420° F.) and/or diesel oil products (boiling between about 300° F. and about 700° F.), are obtained and hence considerations of temperature and pressure will be selected within a range of conversion levels designed to provide the highest selectivity to and maximum yield of such products.

The process of this invention is conducted such that conversion of the olefin feedstock may be carried out in either the liquid-phase or the vapor-phase by contacting the NZ-MS and $C_2$ to $C_{12}$ olefin in a reaction zone, such as, for example, a fixed bed of catalyst, under effective conversion conditions, said catalyst composition being characterized, as synthesized, as comprising one or more of the above-defined non-zeolitic molecular sieve ("NZ-MS") compositions. This process may be conducted in either fixed or fluid bed operation with the attendant benefits of either operation readily obtainable.

The effective conversion conditions employed in carrying out the olefin oligomerization include an effective temperature(s), pressure(s), weight hourly space velocity, contact time(s) and, if employed, an effective amount of diluent. The process is generally carried out at an effective temperature between about 200° F. and 1000° F., preferably between about 300° F. and about 600° F., and at effective pressures ranging between about atmospheric up to about 150 atmospheres or higher, although subatmospheric pressures may be employed. The pressure is preferably between about one atmosphere (0 psig.) and about 100 atmospheres. The weight hourly space velocity (WHSV) of the $C_2$–$C_{12}$ olefin is generally maintained at between about 0.01 $hr^{-1}$ and about 25 $hr^{-1}$ and is preferably between about 0.1 $hr^{-1}$ and about 1.0 $hr^{-1}$.

In most cases it is preferred to employ a diluent in the process, including, but not limited to: $C_1$–$C_4$ paraffins (methane, ethane, propane, isobutane and n-butane); inert gases, such as nitrogen, carbon dioxide; water (and/or steam); and hydrogen. The preferred diluents are paraffinic homologs of the reactant olefins and water.

The effective amount of diluent which may be present in the instant process is not narrowly critical, although specific effective amounts of some diluents may exist, e.g., water. The amount of diluent may vary within the range of from 0 to about 99 weight percent, more preferably between about 1 and about 95 weight percent, based on the weight of total feedstock, i.e., diluent and $C_2$–$C_{12}$ olefins. The amount of diluent is more preferably within the range between about 10 and about 70 weight percent. The NZ-MS catalysts, as above defined for use herein, are generally benefited by co-fed water which has been observed to aid in resisting coking and aging of the NZ-MS containing catalyst under vapor phase conditions, although such effect may not be the only advantage provided by use of water as a diluent.

The effective contact time employed for the oligomerization may vary from seconds to hours and is generally between about 0.05 and about 4 hours and is preferably between about 0.1 and about 2 hours.

It has been found that the NZ-MS class of molecular sieves can be employed in the present process to provide for the selective conversion of the olefin feedstock to oligomer products. In other words, the present process effects the conversion of the olefin feed to dimer, trimer, tetramer, etc., products with high selectivity. The products of the present process thus contain primarily olefin oligomers and little or no light cracked products, paraffins, etc. While not wishing to be bound by any theory, it is believed that this desirable result is brought about by a unique combination of appropriate acid strength, crystal structure, and pore size which form products with minimal hydride transfer activity which would tend to form a large fraction of aromatics and that this unique combination helps prevent catalyst deactivation.

A significant feature of the present process is the liquid phase embodiment involving contact of the olefin feed and the NZ-MS catalyst. Again, while not wishing to be bound by any theory, it is believed that contacting the olefin feed and NZ-MS catalysts in the liquid phase, i.e., the reactant is supercritical and the products are liquid, results in substantially increased catalyst life, since the liquid phase products tend to "wash" higher boiling products from the surface of the catalyst, thus preventing the build-up of such products and the concomitant blocking of active catalyst sites. When both the reactant olefins and the products are in the vapor phase, higher boiling products may tend to deposit on the surface of the NZ-MS catalysts and result in deactivation by blocking catalytically active sites.

The NZ-MS catalysts employed in the instant invention may have a certain proportion of the original cations associated therewith replaced by a wide variety of other cations according to techniques well known in the art. Typical replacing cations include hydrogen, ammonium and alkali and alkaline earth metal cations, including mixtures of the same.

Typical ion exchange techniques involve contacting the particular non-zeolitic molecular sieve (NZ-MS) with a salt of the desired replacing cation or cations. Although a wide variety of soluble salts can be employed, particular preference is given to chlorides, nitrates and sulfates owing to their solubility in water since water is the preferred solvent for such ion exchange techniques. Representative ion exchange techniques are disclosed in a wide variety of patents including U.S. Pat. Nos. 3,140,249; 3,140,251; and 3,140,253. Following contact with the ion exchange solution of the desired replacing cation, the NZ-MS may be washed with water and dried.

One embodiment of this invention resides in the use of a porous matrix with the NZ-MS catalysts previously described, although the use of matrix is optional. The NZ-MS can be combined, dispersed or otherwise intimately admixed with a porous matrix in such proportions that the resulting product contains from 1% to 95% by weight, and preferably from 20% to 80% by weight, of the NZ-MS in the final catalyst composite. The catalysts may be formed by standard catalyst forming techniques including spray-drying, pelleting, extrusion and other suitable conventional means.

The term "porous matrix" includes active or inactive inorganic compositions with which the NZ-MS can be combined, dispersed or otherwise intimately admixed. It is to be understood that the porosity of the compositions employed as a matrix can either be inherent in the particular material or it can be introduced by mechanical or chemical means. Representative matrices which can be employed include metals and alloys thereof, sintered metals and sintered glass, asbestos, silicon carbide aggregates, pumice, firebrick, diatomaceous earths, aluminosilicates and inorganic oxides. Inorganic compositions especially those of a siliceous nature are preferred. Of these matrices, inorganic oxides such as clay, chemically treated clay, silica, silica-alumina, etc., are particularly preferred because of their superior porosity, attrition resistance and stability.

Compositions containing the NZ-MS catalysts and an inorganic oxide can be achieved by several methods wherein the NZ-MS catalyst is admixed with an inorganic oxide while the latter is in a hydrous state such as in the form of hydrosol, hydrogel, wet gelatinous precipitate, or in a dried state, or a mixture thereof. Thus, finely divided NZ-MS can be mixed directly with a siliceous gel formed by hydrolyzing a basic solution of alkali metal silicate with an acid such as hydrochloric, sulfuric, acetic, etc. Mixing of the three components can be accomplished in any desired manner, such as in a ball mill or other such device. The NZ-MS also may be dispersed in a hydrosol obtained by reacting an alkali metal silicate with an acid or alkaline coagulant. The hydrosol is then permitted to set in mass to a hydrogel which is thereafter dried and broken into pieces of desired shape or dried by conventional spray drying techniques or dispersed through a nozzle into a bath of oil or other water-immiscible suspending medium to obtain spheriodally shaped "bead" particles of catalyst such as described in U.S. Pat. No. 2,384,946. The NZ-MS siliceous gel thus obtained may be washed free of soluble salts with water and thereafter dried and/or calcined as desired.

Similarly, the NZ-MS may be incorporated with an aluminoferous oxide. These are gels or hydrous oxides and are well known in the art. They may be prepared, for example, by adding ammonium hydroxide, ammonium carbonate, and the like, to a salt of aluminium, such as aluminum chloride, aluminum sulfate or aluminum nitrate, in an amount sufficient to form aluminum hydroxide which, upon drying, is converted to alumina. The NZ-MS may be incorporated with the aluminoferous oxide while the latter is in the form of hydrosol, hydrogel, or wet gelatinous precipitate or hydrous oxide, or in the dried state.

The inorganic oxide may also consist of raw clay or a clay mineral which has been treated with an acid medium to render it active. The NZ-MS can be incorporated with the clay simply by blending the two and fashioning the mixture into desired shapes. Suitable clays include attapulgite, kaolin, sepiolite, polygarskite, kaolinite, halloysite, plastic ball clays, bentonite, montmorillonite, illite, chlorite, etc.

Other useful matrices include powders of refractory oxides, such as alumina, alpha alumina, etc., having very low internal pore volume. Preferably, these materials are inert with respect to the instant reactions, having substantially no inherent catalytic activity of their own.

Final catalysts which will comprise at least one NZ-MS and, optionally, a matrix, may be heated in steam or in other atmospheres, e.g., air, at the temperature contemplated for conversion or may be heated to operating temperatures initially during use in the process or may be calcined in air, steam, nitrogen, helium flue gas, or other gases not harmful to the catalyst product, at temperatures ranging from about 500° F. to 1600° F. and for periods of time ranging from 1 to 48 hours or more. It is to be understood that the NZ-MS may also be calcined prior to incorporation into the inorganic oxide gel. It is to be further understood that the NZ-MS need not be ion exchanged prior to incorporation into a matrix but can be so treated during or after such incorporation.

The feedstocks useful in the present process may be a feedstock containing one or more of the $C_2$–$C_{12}$ olefins, mixtures thereof and/or mixtures of such with $C_1$–$C_5$ paraffins and/or other diluents. Preferred feedstocks include: ethylene, propylene, butenes and mixture thereof; and a feedstock consisting essentially of $C_2$–$C_5$ linear and/or branched olefins. Further, the feedstock may be an olefin forming feedstock, i.e., a feedstock capable of forming $C_2$–$C_{12}$ linear or branched olefins in situ. The feedstock may, in addition, be any of a number of feeds from other sources including: total gas streams from, for example, an FCC, TCC or Riser cracking unit; a $C_3$ gas fraction from the same or different sources; a $C_4$ mixture from an unsaturated gas plant; the product of a synthesis gas or light alcohol conversion process where such are converted to olefin-containing products; gas streams from a coking unit; and/or may include a partial product recycle of the instant process.

In one embodiment of the instant invention the feedstock from which the $C_2$ to $C_{12}$ olefins are obtained is derived from the conversion of light alcohols and derivative ethers thereof over a ZSM-type zeolite or other methanol to olefins conversion catalyst. Such conversion processes are disclosed in U.S. Pat. Nos. 4,062,905, 4,079,095, 4,079,096, 3,911,041 and 4,049,573, where ZSM-type zeolites are employed as catalysts. The designation "ZSM-type" is meant to refer to those zeolites generally identified in the prior art as "ZSM-n" where "n" is an integer. Further processes for converting methanol and dimethyl ether to olefin products are disclosed in: European Application No. 6,501 (catalyst is HZSM-5); European Application No. 2,492 (catalyst is Mn exchangeed 13X zeolite); German Offen. No. 2,909,928 (catalyst is Fe exchanged "Silicalite"); Angew. Chem. Int. Ed., 19, 2 (1980), 126–7 (catalyst is Mn exchanged chabazite and erionite); South African No. 78/2527 (catalyst is CaH-Fu-1 zeolite); and European Application No. 11,900 (catalyst is boron modified silica).

As aforementioned, olefin-containing feedstocks derived from the conversion of methanol, i.e., light alcohols and derivative ethers thereof, may be advantageously employed in the instant process as the feedstock for the oligomerization of $C_2$ to $C_{12}$ olefins. In such an integrated process the conversion of light alcohols to olefins may be carried out in a first stage or it may be carried out concurrently with the oligomerization process, i.e., the methaol conversion catalyst and the NZ-MS catalyst may be placed in the same reaction zone such that olefin oligomerization occurs as olefin is formed. In general such a two step process provides for the production of hydrocarbon products containing greater than five carbons and comprises:

(a) converting a light alcohol and/or derivative ethers thereof to olefin products at effective conversion conditions over a conversion catalyst, preferably a ZSM-type catalyst; and (b) oligomerizing said olefin products of step (a) at effective process conditions by contacting said olefin products with a NZ-MS catalyst.

EXPERIMENTAL PROCEDURE

The following examples were carried out using a reactor consisting of a 4 inch length of ⅜" stainless steel tubing with ¼" stainless steel tubing feed and product lines. The reactor was immersed in a fluidized-bed sand bath containing heating elements for temperature control. A thermocouple was inserted directly in the catalyst bed to monitor the reaction temperature. Seven grams of the catalyst (powdered form) was used in each example. The feed line was passed through the sand bath to provide a preheat zone prior to introduction of feed to the catalyst bed. The liquid feed flow rate was controlled either by a positive displacement adjustable stroke pump, or by adjusting the setting of a micrometer needle valve by controlling the pressure drop across the valve. When hydrogen was co-fed with the feed the hydrogen flow rate was controlled by a mass flow controller. The system pressure was controlled by a back pressure regulator. Disengagement of the gas and liquid products was carried out at ambient temperature and pressure. The gas products were passed through a dry test meter for flow measurement and then introduced to an on-line gas chromatograph for analysis. The "$C_5{}^+$ product" was the liquid product and that portion of the gas product identified as $C_5{}^+$s and higher carbon number hydrocarbons, i.e. that fraction containing five carbons or greater. In some instances the liquid product was collected, weighed and subjected to a simulated distillation (ASTM D-2887-70T). The feed flow was measured by observing the volume of liquid removed from a high pressure glass feed container over a measured period of time. The percentages employed in the examples are weight percentages.

The NZ-MS compositions employed in the examples were prepared in accordance with the disclosures of the aforementioned copending applications relating thereto.

The following examples are provided to illustrate the invention and are not intended to be limiting thereof:

EXAMPLES 1–4

Examples 1, 2 and 3 show the use of a NZ-MS characterized by crystal structures which have a pore size of about 6.0Å. Examples 1, 2 and 3 show that NZ-MS catalysts containing, in addition to aluminum, phosphorus and oxygen, silicon (SAPO), magnesium (MAPO) or titanium (TAPO), exhibit propylene oligomerization activity with selectivity to $C_5{}^+$ liquid products. Comparative example 4 shows that a catalyst with the same pore size but which does not contain one of the above elements, ($AlPO_4$ containing aluminum, phosphorus and oxygen), is substantially inactive for olefin oligomerization. The designation employed for a given nonzeolitic molecular sieve is consistent with the designations employed in the above identified copending patent applications, wherein its preparation is reported.

The tests were conducted using the apparatus and procedure described in the section entitled "EXPERIMENTAL PROCEDURE" under vapor phase conditions, at 700° F., 25 pounds per square inch gauge (psig), using 7 grams of the designated catalyst and a feed consisting of a mixture of hydrogen and propylene ($C_3$) with about a 2 to 1 molar ratio of hydrogen to propylene. The results of Examples 1 to 4 are summarized below in Table I:

TABLE I

| Example | Catalyst | Time on Stream Hr. | $C_3{}^*$ WHSV hr.$^{-1}$ | $C_3{}^*$ Percent Conversion | $C_5{}^+$ in Converted Product*** |
|---|---|---|---|---|---|
| 1 | SAPO-11 | 4.45 | 0.74 | 70.8 | 78.3 |
| 2 | MAPO-11 | 5 | 1.1 | 50.7 | 78.6 |
| 3 | TAPO-11 | 2.5 | 2.5 | 8.8 | 66.1 |
| 4 | ALPO$_4$-11 | 4.3 | ~1.0 | ~0** | ~0** |

*$C_3$ = propylene
**not capable of quantitative measurement
***Selectivity to $C_5{}^+$ product of converted propylene.

The results set forth in Table I, supra show that NZ-MS catalysts containing silicon, aluminum and phosphorous (SAPO-11), magnesium, aluminum and phosphorous (MAPO-11), titanium, aluminum and phosphorus (TAPO-11), all exhibit catalytic activity and selectivity in the coversion of propylene to $C_5{}^+$ products. The catalyst containing only aluminum and phosphorous (AlPO$_4$-11), although having the same pore size, was inactive, having a propylene conversion of substantially zero.

EXAMPLES 5-8

Examples 5-8 demonstrate that SAPO-11, SAPO-31 and SAPO-34 oligomerize propylene to higher molecular weight products in contrast to a large pore SAPO-5 under the process conditions employed for examples 5 to 8. Of course, the correlation of the olefin feedstock, the selected NZ-MS and effective conversion conditions should be made to provide for formation of the final products of the oligomization process. The examples were conducted under vapor phase conditions at 700° F., 25 psig (50 psig for example 6) using 7 grams of catalyst and a feed consisting of a mixture of hydrogen ($H_2$) and propylene ($C_3$) with a molar ratio of $H_2/C_3$ of about 2 to 1. The results of Examples 5-8 are set forth in Table II.

TABLE II

| Example | Catalyst | Time on Stream (Hr.) | $C_3{}^*$ WHSV hr.$^{-1}$ | $C_3{}^*$ Conversion Percent | $C_5{}^+$ In Converted Product*** |
|---|---|---|---|---|---|
| 5 | SAPO-11 | 4.45 | 0.74 | 70.8 | 78.3 |
| 6 | SAPO-31 | 5.5 | 1.0 | 76.2 | 82.7 |
| 7 | SAPO-5 | 4.3 | 0.98 | ~0** | ~0** |
| 8 | SAPO-34 | 2.3 | 0.53 | 41.6 | 19.5 |

*$C_3$ = propylene
**not capable of quantitative measurement
***Selectivity to $C_5{}^+$ product of converted propylene.

It is clear from the results set forth in Table II that the large pore SAPO-5 was inactive as an oligomerization catalyst under the process conditions employed for example 7. This apparent inactivity may be a result of rapid deactivation, e.g., coking, following introduction of the propylene feedstock. SAPO-34 showed activity for propylene conversion, but produced primarily gaseous hydrocarbons with carbon number less than five ($C_5{}^-$). Correlation of the process conditions or modification of SAPO-34 and SAPO-5 may provide for higher conversions to the desired products. SAPO-11 and SAPO-31 and, accordingly, NZ-MSs having the X-ray patterns of Tables A and B are within the most preferred class of NZ-MS catalysts employable herein, since both SAPO-11 and SAPO-31 catalysts gave high propylene conversion and high selectivity to $C_5{}^+$ liquid products.

EXAMPLES 9 AND 10

Examples 9 and 10 demonstrate the use of diluents, e.g., propane or $H_2O$, to influence conversion and product selectivity, and also to illustrate the differences in the vapor phase and liquid phase operation on propylene conversion and on product selectivity.

(a) Effect of Water Diluent

Example 9 was carried out under vapor phase conditions at 700° F. using 7 grams of a NZ-MS catalyst. The NZ-MS catalyst was SAPO-11. The process was carried out by conducting a test without co-fed water and with co-fed water. Each test (tests "a" and "b") was conducted with a fresh catalyst charge. The results of test "a" and "b" are set forth in Table III.

TABLE III

| Test | Catalyst | Time on Stream (Hr.) | Pressure (psig) | Feed[1] Mole Ratio $H_2/C_3/H_2O$ | $C_3$ WHSV (hr$^{-1}$) | $C_3$ Percent Conversion[2] | $C_5{}^+$ in Converted Product[3] | Refractive Index[4] |
|---|---|---|---|---|---|---|---|---|
| a | SAPO-11 | 4.45 | 25 | 2/1/0 | 0.74 | 70.8 | 78.3 | 1.4709 |
| b | SAPO-11 | 4.74 | 50 | 2/1/1 | 0.76 | 73.7 | 90.6 | 1.4131 |

[1]$H_2$ = hydrogen; $C_3$ = propylene; $H_2O$ = water.
[2]weight percent of propylene converted.
[3]weight percent $C_5{}^+$ in converted product $C_5{}^+$, i.e., selectivity.
[4]Refractive Index, $N_D$ 25° C., of the liquid $C_5{}^+$ product at 25° C.

The data in Table III show that when water was employed as the diluent it provided an increase in the propylene conversion, and a substantial increase in selectivity of propylene to the $C_5{}^+$ products, i.e., products containing more than five carbons. Simulated distillations of the liquid products were conducted according to ASTM method D-2887-70T. The weight percent (wt %) of the distilled product was plotted as a function of distillation temperature for tests "a" and "b" and these plots are set forth in FIG. 1. FIG. 1 demonstrates that addition of water as a diluent to the feed dramatically changed the distribution of the liquid products. In "test b" of Table III the use of co-fed water gave a product having 56% of the $C_5{}^+$ product boiling between about 160° and about 170° F. The boiling point and refractive index of the liquid product showed that with co-fed water as a diluent that the liquid product was predominantly $C_6$ olefins. In contrast, the boiling distribution for the liquid product of "test a" (without co-fed water) shows no predominant quantity of any distinct hydrocarbon compound with the boiling distribution demonstrating that a wide mixture of hydrocarbon compounds were produced. The refractive index of the liquid product of "test a" indicates that the product contained a higher percentage of aromatic products than the liquid products of test "b".

b. Effect of Propane Diluent

Example 10 was conducted under liquid phase conditions using 7 grams of catalyst. The term "liquid phase" is employed in this example to indicate that the products were in the liquid phase and propylene and the diluent (propane) may have been in the vapor phase in a supercritical state. The NZ-MS catalyst was SAPO-11. The process was carried out both without propane and with propane as a diluent at two different weight hourly space velocities (tests "a", "b", and "c"). The results of "tests a, b and c" are set forth in Table IV. The feedstocks, both with and without propane, employed in "tests a, b and c" were tested sequentially in the same run with the same charge of SAPO-11 catalyst.

TABLE IV

| Test | Time on Stream (Hr.) | Feed[1] Mole Ratio | Temp. °F. | WHSV (hr.$^{-1}$) | $C_3$ Percent Conversion[2] | $C_5{}^+$ in Converted Product[3] | Refractive Index[4] |
|---|---|---|---|---|---|---|---|
| a | 21.3 | 0/1 | 400 | 0.95 | 95.9 | 99.88 | 1.4263 |
| b | 35.6 | 2/1 | 400 | 0.85 | 48.8 | 98.17 | 1.4251 |
| c | 56.5 | 2/1 | 550 | 0.55 | 94.7 | 98.5 | 1.4234 |

[1]mole ratio of propane to propylene ($C_3$).
[2]weight percent of propylene ($C_3$) converted.
[3]weight percent $C_5{}^+$ converted product $C_5{}^+$.
[4]Refractive Index, $N_D$ 25° C., of the liquid $C_5{}^+$ product at 25° C.

The data in Table IV demonstrate that when propane is employed as a diluent at a conversion temperature of 400° F. that it had a significant effect on propylene conversion. The propylene conversion decreased from 95.9% without propane diluent to 48.8% when the propane diluent was employed. The $C_5{}^+$ selectivity was comparable both with and without the propane diluent. The refractive index of the liquid product was also comparable both with and without use of the propane diluent. An increase in temperature from 400° F. to 550° F. and a reduction in the WHSV from 0.95 hr.$^{-1}$ to 0.55 hr.$^{-1}$ gave a propylene conversion of 94.7%.

Figure 2:
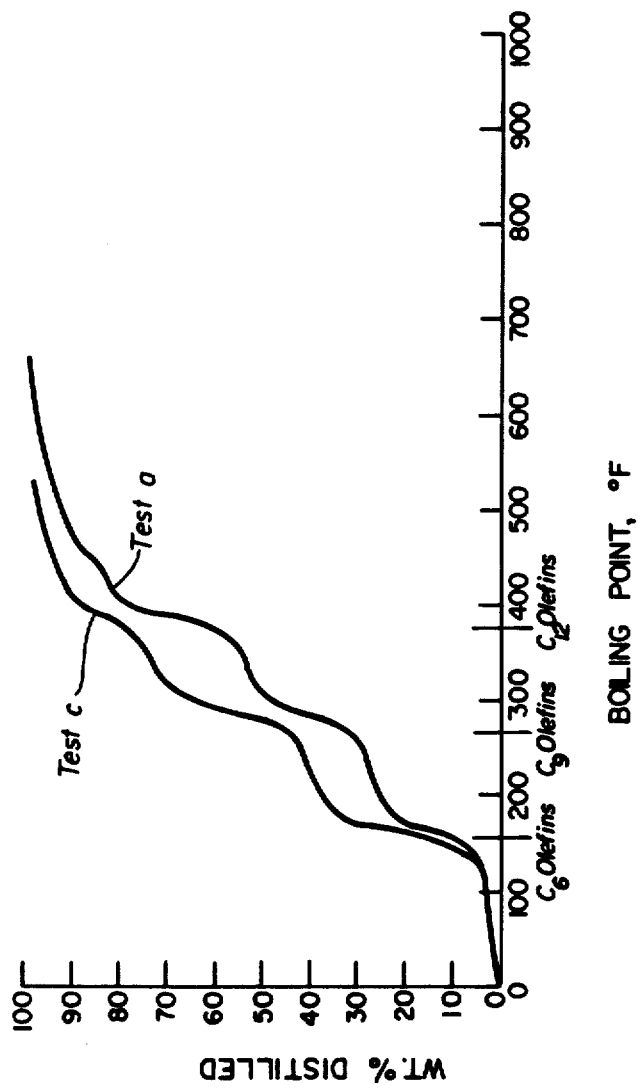
FIG. 2 shows the effect of propane on the product distribution of the instant invention.

Simulated distillations (ASTM D-2887-70T) of the liquid products produced above both without and with propane diluent (tests "a" and "c", respectively) are presented in FIG. 2. The simulated distillations demonstrate that the addition of propane as a diluent resulted in a shift to lighter boiling products. The propane diluent resulted in an increase in the amount of liquid product boiling at temperature corresponding to $C_6$ and $C_9$ olefins and a reduction in the products boiling at a temperatures corresponding to $C_{12}$ olefins. In addition, the liquid product boiling above 420° F. was reduced from about 18% wt. to about 8% wt. of the liquid product as a result of the addition of the propane diluent. The production of lighter products in the presence of propane diluent was actually greater than indicated by FIG. 2, since some $C_6$ products were contained in the gas product as a result of the gas product flowrate employed when propane is employed as the diluent and tends to strip volatile $C_6$ products from the liquid product.

c. Comparison of Vapor and Liquid Phase Operation

Examples 9 and 10 show that liquid phase operation tends to require higher pressures than that employed for vapor phase operation, and, accordingly, higher reactant concentrations. As a result of the higher process pressures, higher propylene conversions can generally be obtained at much lower temperatures under liquid phase conditions, as compared to the temperatures employed for vapor phase operation. The higher propylene conversions obtained under liquid phase conditions may be due to both higher reactant concentrations and to a solubilizing effect under liquid phase conditions on higher molecular weight reaction products which may otherwise be strongly adsorbed on the NZ-MS catalyst. Adsorbtion of such higher molecular weight reaction products on the NZ-MS may inhibit access of the olefin reactants to active sites of the NZ-MS catalyst.

The use of water as the diluent in the vapor phase process of Example 9 showed a greater effect on product selectivity than did the use of propane as the diluent in the liquid phase process of Example 10, although in both cases the presence of diluent resulted in the production of lighter products within the $C_5{}^+$ fraction. The boiling distributions shown in FIGS. 1 and 2 for the diluent containing feedstocks show a greater $C_6$ olefin fraction under vapor phase conditions than obtained under liquid phase conditions. Increased quantities of $C_9$ and $C_{12}$ olefins are shown under the liquid phase process conditions of Example 10.

EXAMPLE 11

This example was carried out under vapor phase conditions at 700° F., 25 psig., 0.85±0.15 WHSV for 200-300 minutes, and demonstrates that variations in the synthesis of the NZ-MS may result in changes in the catalyst activity of the NZ-MS as an olefin oligomerization catalyst. SAPO-11 was prepared using two synthesis procedures wherein the first procedure employed one organic templating agent and the second procedure employed two organic templating agents. The SAPO-11 prepared using a single template employed di-n-propylamine in an aqueous methanol media. This SAPO-11 product will be referred to herein as single template SAPO-11 or as S-SAPO-11. The SAPO-11 prepared using two templates employed di-n-propylamine (DPA) and tetra-butylammonium hydroxide (TBA) in an aqueous methanol media and will be referred to herein as dual template SAPO-11 or as D-SAPO-11. D-SAPO-11 was prepared from a reaction mixture having the following reaction mixture expressed in terms of molar oxide ratios:

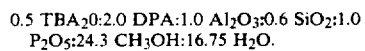

S-SAPO-11 and D-SAPO-11 were tested for olefin oligomerization under substantially the same conditions of 700° F., 0.74–0.94 WHSV, and 25 psig with propylene as the selected olefin. The reaction conditions and the results of these tests are set forth in Table V. Product samples were collected over the first 250-270 minutes of each test.

The data in Table V indicate that D-SAPO-11 with 86.3% propylene conversion was more active, i.e., gave a high conversion of olefin to products than that obtained using the single template S-SAPO-11, which had a 70.8% conversion. The selectivities to $C_5{}^+$ liquid products for both SAPO-11's were similar being about 77-78%. The weight percent of product boiling above 420° F. was lower for D-SAPO-11, 1.8%, compared with the 4.5% obtained for S-SAPO-11. The gaseous products formed using D-SAPO-11 had about twice the saturates (7.5%) obtained using S-SAPO-11 (3.7%).

EXAMPLE 12

Example 12 demonstrates the differences obtained by use of NZ-MS catalysts as compared with the aluminosilicate catalyst disclosed in U.S. Pat. No. 4,257,885, referred to herein as Catalyst A. Catalyst A had a $SiO_2$ to $Al_2O_3$ ratio of 43.3 and was employed as an olefin oligomerization catalyst under vapor phase conditions.

Example 12 was carried out under vapor phase conditions of 700° F., 25 psig, 0.85±0.15 WHSV for 200–300 minutes on stream. The results of these tests are reported in Table V under the heading "Catalyst A."

Under these conditions, Catalyst A had a 81.6% propylene conversion with a 37.2% $C_5^+$ selectivity. The $C_5^+$ liquid product contained about 12 percent by weight of components boiling above 420° F. (gasoline range). The remaining products were less than $C_5$ ($C_5^-$) consisting of about 52% saturates, i.e., light paraffins.

SAPO-11 was employed under similar reaction conditions as employed for Catalyst A. The reaction conditions and results for SAPO-11 are set forth in Table V under the heading "S-SAPO-11". The preparation of "S-SAPO-11" is set forth in example 11.

Comparison of the results for Catalyst A and the SAPO-11s of Table V shows that SAPO-11 catalysts gave approximately the same propylene conversion (70–86%) as Catalyst A, but the selectivity to $C_5^+$ products more than doubled (63% to 78.3%) as compared to those obtained with Catalyst A (37.2%). Several advantages were demonstrated by the use of SAPO olefin oligomerization catalysts. First, the total $C_5^+$ yield was about doubled. Second, the production of low value light paraffins was drastically reduced using the SAPO catalysts with the yield of light paraffins being 2–7% for SAPO catalysts as compared to the 52% obtained by use of Catalyst A. Third, the liquid product obtained using SAPO catalysts had a narrower boiling range than the liquid product obtained by use of Catalyst A. Specifically, the fraction of the product boiling above 420° F. in the $C_5^+$ product is reduced from the 12% obtained with Catalyst A to only about 4.5% or less when a SAPO catalyst is employed.

EXAMPLE 13

SAPO-31 (single organic-templating agent) was evaluated as an olefin oligomerization catalyst and the results of this evaluation compared with the results obtained using the SAPO-11 compositions of Example 11. Testing conditions were substantially the same as employed in Example 11, except that SAPO-31 was evaluated at a pressure of 50 psig instead of at the 25 psig employed in Example 11. The reaction conditions and results are set forth in Table V.

SAPO-31 gave a propylene conversion of 76.2% and a $C_5^+$ selectivity of 82.7%. The boiling distribution of the product was narrow with only 1.7% of the liquid product boiling above 420° F. with only a 2.02% liquid paraffin yield based on the weight of the feed.

TABLE V[1]

| Example | Catalyst A 12 | S-SAPO-11 11 | D-SAPO-11 11 | SAPO-31 13 |
|---|---|---|---|---|
| % Conversion | 81.6% | 70.8% | 86.3% | 76.2 |
| Selectivity to: | | | | |
| $C_5^-$: | 62.8% | 21.7% | 23.0% | 17.3% |
| $C_5^+$: | 37.2% | 78.3% | 77.0% | 82.7% |
| 420° F.+ in $C_5^+$ | 12.0% | 4.5% | 1.8% | 1.7% |
| % Olefins in $C_5^+$ | 0% | 55.3% | 46.4% | 50% |
| % $C_5^-$ saturates | 51.9% | 3.71% | 7.5% | 2.02% |
| CONDITIONS: | | | | |
| Temperature (°F.) | 700° F. | 700° F. | 700° F. | 700° F. |
| WHSV (Hr.$^{-1}$) | 0.90 | 0.74 | 0.94 | 1.04 |
| Pressure (psig.) | 25 psig | 25 psig | 25 psig | 50 psig |
| Time (minutes) | 209 min. | 267 min. | 250 min. | 330 min. |

[1] All percentages are weight percent based on the weight of feed converted to products.

EXAMPLE 14

The conversion of 2-butene to $C_5^+$ liquid hydrocarbon products using SAPO-11 was evaluated under liquid phase conditions using a pressure of 900 psig and an average temperature of 544° F. with a 7 gram charge of catalyst. The feedstock was pure 2-butene. No analysis of the gas product was performed.

The results of the analysis of the liquid product are shown in Table VI. The refractive index of the liquid product indicates that highly olefinic liquid products were formed.

TABLE VI

| Example | Catalyst | Time on Stream (Hrs.) | 2-Butene WHSV (Hr.$^{-1}$) | Conversion (%) | $C_5^+$ Product[1] | Refractive[2] Index |
|---|---|---|---|---|---|---|
| 14 | SAPO-11 | 12.75 | 1.43 | >82.9 | >82.9 | 1.4354 |

[1] The weight percent of $C_5^+$ liquid product based on weight of feedstock 2-butene converted.
[2] Refractive index, $N_D$ 25° C., at 25° C.

What is claimed is:

1. The process for the oligomerization of linear and-/or branched chain $C_2$ to $C_{12}$ olefins which comprises contacting said olefins at effective process conditions for said oligomerization with an oligomerization catalyst comprising at least one molecular sieve selected from the group consisting of FAPO, TAPO and MeAPO characterized by an adsorption of triethylamine less than 5 percent by weight at a pressure of 2.6 torr and a temperature of 22° C.

2. The process of claim 1 wherein said "NZ-MS" is FAPO.

3. The process of claim 1 wherein said "NZ-MS" is TAPO.

4. The process of claim 1 wherein said "NZ-MS" is MeAPO.

5. The process of claim 4 wherein said "NZ-MS" is MnAPO.

6. The process of claim 4 wherein said "NZ-MS" is CoAPO.

7. The process of claim 4 wherein said "NZ-MS" is MAPO.

8. The process of claim 4 wherein said "NZ-MS" is ZnAPO.

9. The process of claim 1 wherein said molecular sieve is at least one selected from the group consisting of TAPO-11, MeAPO-11, MeAPO-31, and TAPO-31.

10. The process of claim 1 wherein said "NZ-MS" is characterized by an adsorption of cyclohexane of at least 2 percent by weight at a pressure of 90 torr and a temperature of 24° C.

11. The process of claim 1 or 5 wherein said "NZ-MS" has an x-ray diffraction pattern characterized by Table A.

12. The process of claim 1 or 5 wherein said "NZ-MS" has the x-ray diffraction pattern characterized by Table B.

13. The process of claim 1 or 5 wherein said "NZ-MS" has the x-ray diffraction pattern characterized by Table C.

14. The process of claim 1 for the oligomerization of an olefin feedstock wherein such process is carried out at a temperature between about 200° F. and about 1000° F., a WHSV between about 0.01 and about 25, and at a pressure between about 1 atmosphere and about 150 atmospheres.

15. The process of claims 1 or 14 wherein said olefin feedstock comprises of $C_2$ to $C_5$ olefins.

16. The process of claim 1 wherein said olefin feedstock contains an effective amount of a diluent selected from the group consisting of $C_1$–$C_{14}$ paraffins, nitrogen, carbon dioxide, hydrogen, water and mixtures thereof.

17. The process of claim 16 wherein said diluent is water.

18. The process of claim 17 wherein said mole ratio of water to olefin feedstock is in the range of about 1 and about 95 percent by weight.

19. The process of claim 1 wherein said olefin comprises ethylene.

20. The process of claim 1 wherein said olefin comprises propylene.

21. The process of claim 10 wherein said olefin feedstock comprises of $C_2$–$C_5$ olefins.

22. The process of claim 1 wherein said olefin feedstock comprises a mixture of ethylene, propylene and butylene.

23. The process of claim 1 wherein said olefin feedstock comprises a mixture of ethylene and propylene.

24. The process of claim 1 wherein said olefin feedstock comprises a mixture of propylene and butylene.

25. The process of claim 15 wherein at least 20 percent by weight of the $C_2$ to $C_5$ olefin is converted to $C_5{}^+$ products.

26. The process of claim 25 wherein the $C_5{}^+$ products boil between 80° F. and 420° F.

27. The process of claim 25 wherein the $C_5{}^+$ products boil between about 300° F. and about 700° F.

28. The process of claim 1 wherein the process is carried out in the vapor phase.

29. The process of claim 1 wherein the process is carried out in the liquid phase.

30. The process for the production of hydrocarbon products containing greater than five carbons comprising:
(a) converting light alcohols and derivatives thereof to $C_2$ to $C_{12}$ olefin products at effective conversion conditions over a conversion catalyst; and
(b) contacting said olefin products of part (a) at effective olefin oligomerization conditions with a NZ-MS catalyst to form hydrocarbon products.

31. The process of claim 30 wherein the conversion catalyst of step (a) is a ZSM-type zeolite.

* * * * *